United States Patent [19]

Leung-Toung et al.

[11] Patent Number: 5,723,618
[45] Date of Patent: Mar. 3, 1998

[54] 1,4-DIHYDROPYRIDINES, N-SUBSTITUTED BICYCLIC 4-HYDROPYRIDINES, AND BICYCLIC N-SUBSTITUTED 4,5-DIHYDROPYRIDINES

[75] Inventors: Regis Chung Soon Hin Leung-Toung; Khashayar Karimian; Tim Fat Tam, all of Mississauga, Canada

[73] Assignee: Apotex, Inc., Ontario, Canada

[21] Appl. No.: 729,017

[22] Filed: Oct. 10, 1996

[30] Foreign Application Priority Data

Nov. 1, 1995 [NZ] New Zealand ............... 280378

[51] Int. Cl.$^6$ ............................................. C07D 211/86
[52] U.S. Cl. ........................... 546/121; 546/321; 544/105
[58] Field of Search ........................ 546/121, 321; 544/105

[56] References Cited

U.S. PATENT DOCUMENTS

| 4,380,547 | 4/1983 | Materne | 424/270 |
|---|---|---|---|
| 4,572,909 | 2/1986 | Campbell et al. | 514/356 |
| 5,234,821 | 8/1993 | Achiwa | 435/41 |
| 5,389,654 | 2/1995 | Furlan et al. | 514/356 |
| 5,438,145 | 8/1995 | Furlan et al. | 546/321 |
| 5,519,012 | 5/1996 | Ferčej-Temeljotov et al. | 514/58 |

FOREIGN PATENT DOCUMENTS 1253865  5/1989  Canada.

OTHER PUBLICATIONS

Satoh et al., "Studies on Nilvadipine. III. Synthesis of ..." Chem. Pharm. Bull., (1992), vol. 40(7), pp. 1799–1807.

*Primary Examiner*—Mukund J. Shah
*Assistant Examiner*—Tamthom T. Ngo
*Attorney, Agent, or Firm*—Nixon & Vanderhye P.C.

[57] ABSTRACT

The invention relates to a novel process to prepare 1,4-dihydropyridines and in particular amlopidine and in novel intermediates obtained during the synthesis of the 1,4-dihydropyridines which have potential activity as antihypertensive agents.

12 Claims, No Drawings

1,4-DIHYDROPYRIDINES, N-SUBSTITUTED BICYCLIC 4-HYDROPYRIDINES, AND BICYCLIC N-SUBSTITUTED 4,5-DIHYDROPYRIDINES

FIELD OF INVENTION

The invention relates to a novel process to prepare 1,4-dihydropyridines and in particular amlopidine.

In another aspect the invention relates to the preparation of novel 1,4-dihydropyridines and novel intermediates obtained during the synthesis of the 1,4-dihydropyridines.

In a further aspect of the invention relates to novel 1,4-dihydropyridines, novel bicyclic N-substituted 4,5 dihydropyridines and novel N-substituted bicyclic 4-hydropyridines.

BACKGROUND OF THE INVENTION

Dihydropyridines derivatives such as nicardipine, nifedipine and nimodipine are used for the treatment of angina. Dihydropyridines have been extensively examined as calcium channel blockers and recently amlodipine was found to have activity as an anti-ischaemic and hypertensive agents.

Canadian Patent 1,253,865 teaches the preparation of 1,4-dihydropyridines having a substituted-amino group at the 2 position and among them amlodipine. According to one aspect of the invention there is provided a 1,4-dihydropyridine of the formula I:

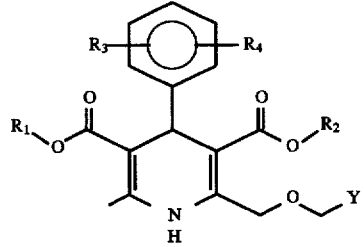

(I)

or the pharmaceutically acceptable salt there of, wherein $R_1$ and $R_2$ may be lower alkyls; $R_3$ is hydrogen, or halogens; $R_4$ is hydrogen, or halogens; Y is selected from the group of formula II, III, V or VI.

$-CH_2NR_5R_6$  II

 III

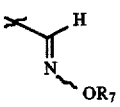

 V

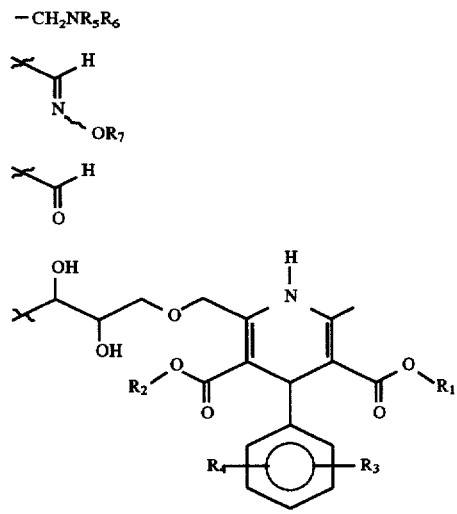 VI wherein in formula II $R_5$ is hydroxy, alkoxy, or 1-alkoxyalkyloxy when $R_6$ is hydrogen.

$R_6$ is hydroxy, alkoxy, or 1-alkoxyalkyloxy when $R_5$ is hydrogen.

wherein in formula III $R_7$ is hydrogen, lower alkyls, or 1-alkoxyalkyls.

The 1,4-dihydropyridines are prepared by removal of the amino-protecting group from the corresponding amino-protected pyridine or by reducing the corresponding azido compound to obtain the amine. The amino-protected pyridines are prepared by the Hantzsch synthesis. The overall yield for the preparation of amlodipine is in the range of 12% to 24%.

According to a further aspect of the invention there is provided a process for the preparation of 1,4-dihydropyridine derivative of the formula I or a pharmaceutically acceptable salt thereof, wherein $R_1$ and $R_2$ are lower alkyls; $R_3$ is hydrogen, or halogens; $R_4$ is hydrogen, or halogens; Y is selected from the group of formula II, III, V, or VI $-CH_2NR_5R_6$  II

 III

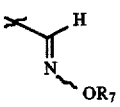

 V

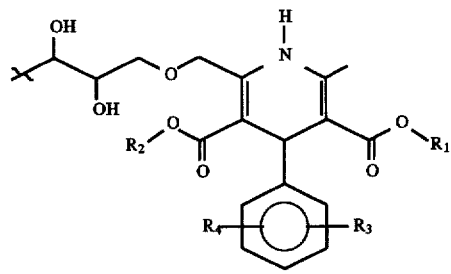 VI wherein $R_5$ is hydrogen, hydroxy, or alkoxy when $R_6$ is hydrogen $R_6$ is hydrogen, hydroxy, or alkoxy when $R_5$ is hydrogen $R_7$ is hydrogen, $C_1$–$C_4$ alkyl, 1-alkoxyalkyl which comprises conversion of a compound of formula ID wherein $R_1$ and $R_2$ are lower alkyls; $R_3$ is hydrogen, or chloro; $R_4$ is hydrogen, or chloro to a compound of formula I in which $R_1$ and $R_2$ are lower alkyls; $R_3$ is hydrogen, or chloro; $R_4$ is hydrogen, or chloro; Y is selected from the group of formula II wherein $R_5$ is alkoxy, 1-alkoxy-1-alkylalkoxy, hydrogen, and $R_6$ is alkoxy, 1-alkoxy-1-alkylalkoxy, hydrogen.

wherein the conversion process includes one or more of the following steps:

(a) converting a compound of formula ID wherein $R_1$ and $R_2$ are lower alkyls; $R_3$ is hydrogen, or chloro; $R_4$ is hydrogen, or chloro to a compound of formula I in which $R_1$ and $R_2$ are lower alkyls; $R_3$ is hydrogen, or chloro; $R_4$ is hydrogen, or chloro, $R_5$ is hydrogen, $R_6$ iscyanohydride hydrogen by reductive amination using ammonium acetate and sodium in a protic solvent such as methanol.

(b) converting a compound of formula ID wherein $R_1$ and $R_2$ are lower alkyls; $R_3$ is hydrogen, or chloro; $R_4$ is hydrogen, or chloro to a compound of formula I in which $R_5$ and $R_6$ are hydrogens and $R_1$, $R_2$, $R_3$ and $R_4$ are defined by:

(i) reacting a compound of formula ID with hydroxylamine hydrochloride and base to give an oxime of formula IB wherein $R_7$ is hydrogen; or (ii) converting an oxime of formula IB wherein $R_7$ is hydrogen with acid or base and an alkylation agent to an oxime of formula IB wherein $R_7$ is alkyl, 1-alkoxyalkyl; or (iii) reacting an oxime of formula IB wherein $R_7$ is alkyl, or hydrogen with sodium cyanohydride in acetic acid and dichloromethane, or ammonium formate in methanol in the presence of palladium hydroxide on charcoal, to give a compound of formula IA wherein $R_5$ is hydrogen, or alkoxy when $R_6$ is hydrogen; and (c) converting a compound of formula I into a pharmaceutically acceptable salt.

In the present application, the 1,4-dihydropyridines derivatives are prepared by reductive amination of the corresponding aldehyde as follows:

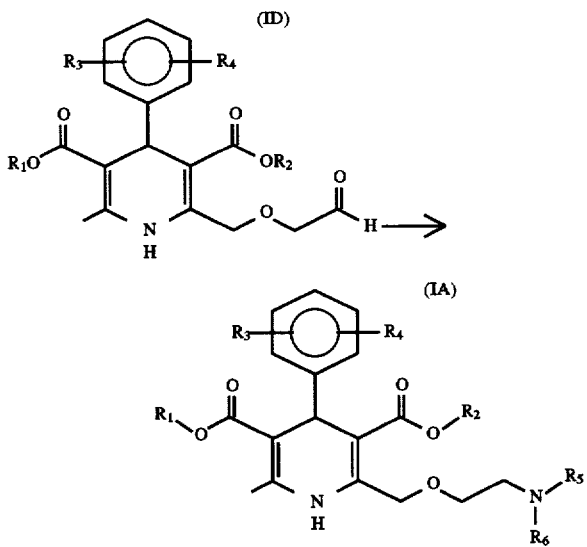

The present process offers major advantages over the existing procedures.

First, the dihydropyridine derivatives are formed in good yields employing easily available precursors. Our overall yield is far greater than the prior art, ie. 46% for amlodipine.

Second, two different routes are used to generate the amine derivative (IA) in good yields. The aldehyde can be converted to the amine derivative in high yield by reductive amination, or alternatively it may be first converted to the oxime derivative which is crystalline and can be purified by conventional means without chromatography. Reduction of the oxime to the amine can be achieved in high yield.

Third, there is no deprotection of amino functionality in the last step of the synthesis involving the use of highly toxic material such as hydrazine.

Forth, use of highly toxic and potentially explosive azide (for protection of the amine function) is avoided.

Fifth, our syntheses provide access to a series of hitherto unknown di- and hydropyridines with potential therapeutic value.

According to the present invention a novel process for the preparation of 1,4-dihydropyridines derivatives of the formula (IA) and their pharmaceutically acceptable salt is provided.

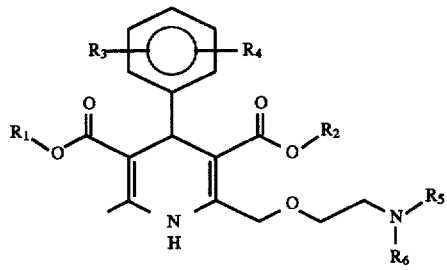

wherein:

$R_1$ and $R_2$ are each independently lower alkyl, aryl or arylalkyl;

$R_5$ is hydrogen, hydroxy, lower alkyl or 1-alkoxyalkyloxy;

$R_6$ is hydrogen;

$R_3$ and $R_4$ are each independently hydrogen or halogen. Halogen includes fluoro, chloro, bromo or iodo;

Lower alkyl including both straight and branched chain radicals of less than 5 carbon atoms.

When $R_1$ and $R_2$ are aryls or arylalkyls, phenyl or benzyl is preferred.

The compounds of formula (IA) are prepared by the conversion of the corresponding aldehyde (ID) to the amine derivative as illustrated by the following scheme:

ID→IA

The reductive amination shown above can be direct or through the formation of the corresponding oxime (IB) as follows:

ID→IB→IA wherein $R_7$ is hydrogen, lower alkyl or 1-alhoxyalkyl. A preferred 1-alhoxyalkyl is 1-methoxy-1-methylethyl.

The direct reductive amination is preferably conducted in the presence of ammonium acetate and sodium cyanohydride.

When the oxime (IB) is converted to the corresponding 1,4dihydropyridine derivatives of formula IA it is preferably done:

(a) in the presence of ammonium formate and palladium hydroxide; or (b) in the presence of acetic acid with sodium cyanohydride.

Preferred compounds (IA) of the invention are those in which:

$R_1$ is preferably lower alkyls and more preferably $C_1$–$C_2$ alkyl and most preferably methyl, or ethyl;

$R_2$ is preferably lower alkyls and more preferably $C_1$–$C_2$ alkyl and most preferably methyl, or ethyl;

$R_3$ is preferably hydrogen, or fluoro, or chloro, more preferably chloro, and most preferably chloro at the 2-position when $R_4$ is hydrogen; or $R_4$ is preferably hydrogen, or halogen, more preferably chloro, and most preferably chloro at the 2 position when $R_3$ is hydrogen;

$R_5$ is preferably a hydrogen, hydroxy or alkoxy and more preferably a hydroxy when $R_6$ is hydrogen;

$R_6$ is preferably hydrogen, lower alkyl, 1-alkoxyalkyl and more preferably a hydroxy when $R_5$ is hydrogen. Preferred salt forming acid for compound of formula IA are those containing carbon double bonds such as maleic acid, p-toluenesulfonic acid, benzenesulfonic acid and most preferably benzenesulfonic acid.

The precursors or intermediates in the preparation of the 1,4-dihydropyridines derivatives of formula (IA) are prepared in accordance with:

(i) the equation below:
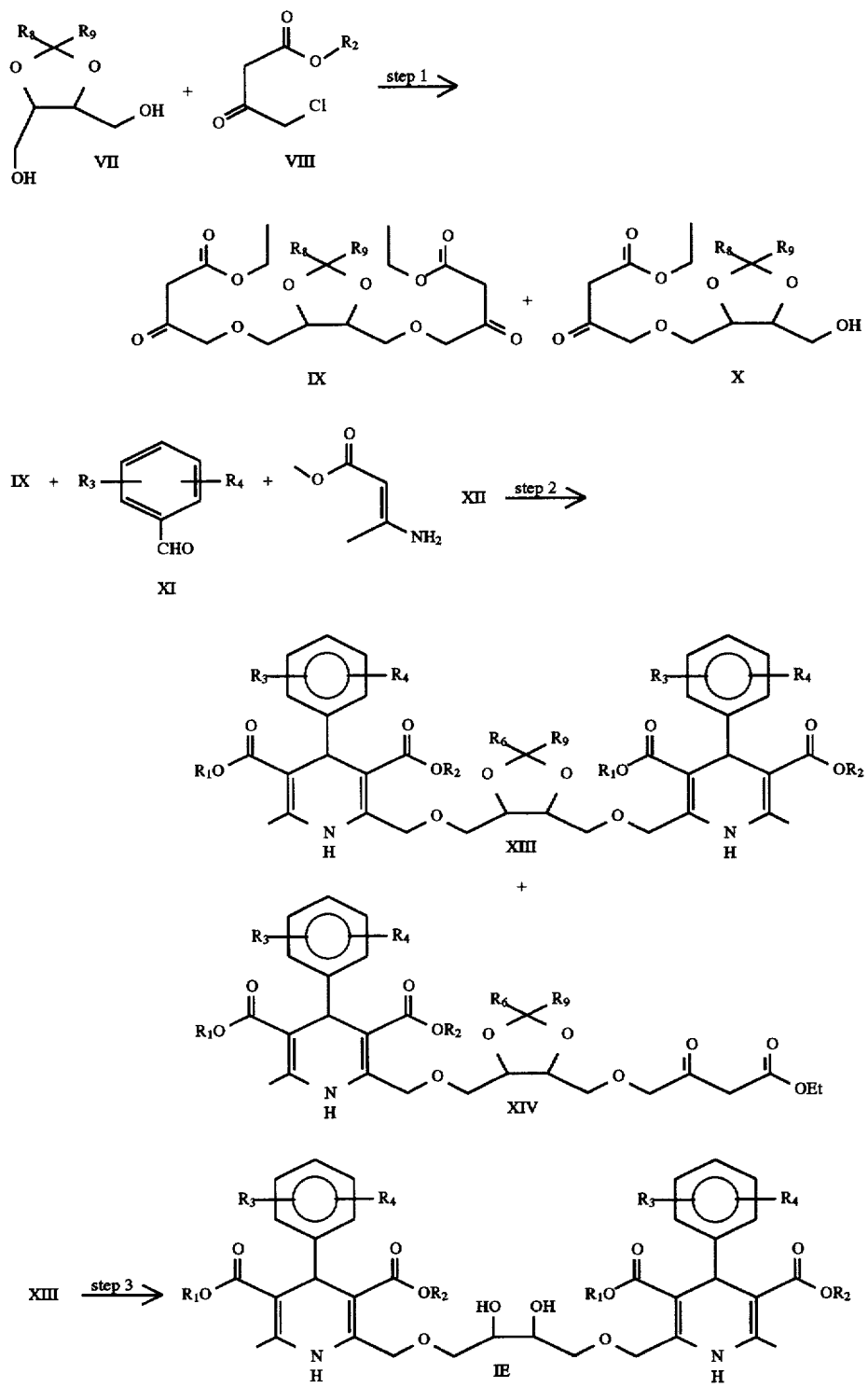

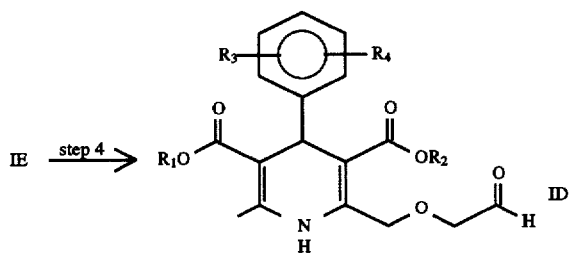

wherein $R_8$ and $R_9$ are each independly hydrogen, $C_1$–$C_4$ alkyl or phenyl or $R_8$ and $R_9$ may be connected together to form an alkylene bridge of 4 to 5 carbon atoms.

In the process shown in Scheme I one equivalent of the diol (VII) is reacted with four to six equivalents of sodium hydride in an inert solvent such as tetrahydrofuran or dimethyl formamide at 25° to 65° C., preferably 65° C., and the resulting dialkoxide is reacted with the ketoester (VIII) to give compounds (IX and X). The products of formula (IX and X) can be isolated and purified by conventional procedures such as column chromatography. The resulting dimer (IX), aldehyde (XI) and the amine (XII) are heated in a suitable solvent such as methanol or ethanol, preferably under reflux for a period of 24 hrs or until such time reaction is complete. The products (XIII) and (XIV) are isolated by conventional means. The protected diol (XIII) is treated with a protic solvent such as methanol in the presence of catalytic amount of p-toluenesulfonic acid, preferably at room temperature for a period of two to ten hours, preferably ten hours to give the diol (IE) which is isolated by conventional means. The resulting diol (IE) is dissolved in a water miscible solvent such as methanol, or ethanol, or dioxane, preferably methanol and treated with 1 to 1.5 equivalent of sodium metaperiodate for a period of 5 to 30 minutes, preferably 10 minutes to give the aldehyde (ID). The aldehyde (ID) is isolated by conventional means such as extraction and solvent removal; or (ii) the following representation:

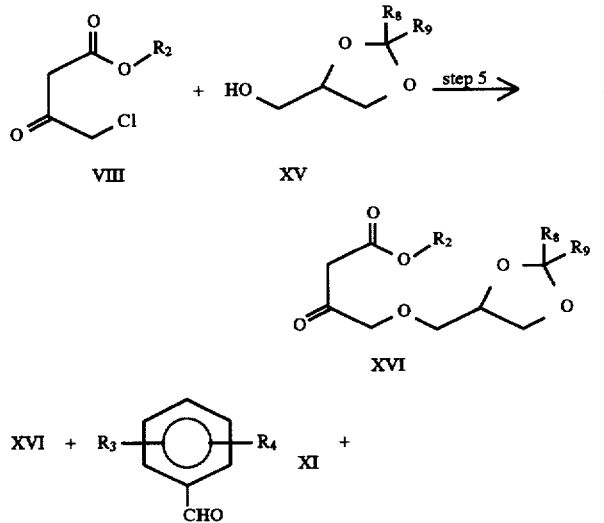

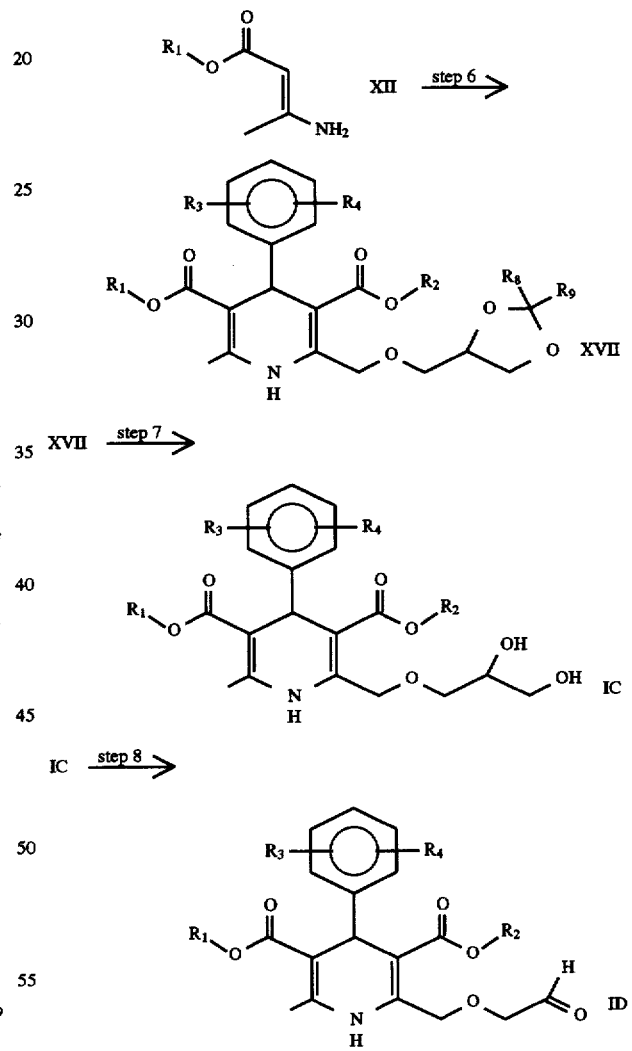

In the process shown in Scheme II a ketoester (VIII) is reacted with two to four equivalents of sodium hydride and one equivalent of a solketal derivative of formula (XV) in an inert solvent such as tetrahydrofuran or dimethyl formamide at 25°to 65° C., preferably 25° C. to give compound (XVI). The product of formula (XVI) can be isolated and purified by conventional procedures such as column chromatography or vacuum distillation, see Alker, D., J. Med. Chem. 1991, 34, 19. The protected diol (XVI), the aldehyde (XI) and the amine (XII) are heated in a suitable solvent such as methanol or ethanol, preferably under reflux for a period of 24 hrs or until such time the reaction is complete. The resulting dihydropyridine (XVII) is isolated by conventional means. Compound of formula (XVII) is treated with a protic solvent such as methanol in the presence of catalytic amount of p-toluenesulfonic acid, preferably at room temperature for a period of two to ten hours, preferably ten hours to give the diol (IC). The product is isolated by conventional means. The resulting diol (IC) is dissolved in a water miscible solvent such as methanol, ethanol, dioxane, preferably methanol and treated with 1 to 1.5 equivalent of sodium metaperiodate for a period of 5 to 30 minutes, preferably 10 minutes to give the aldehyde (ID). The product aldehyde (ID) is isolated by conventional means such as extraction and solvent removal.

The reaction of (ID) to produce (IA) is depicted below:

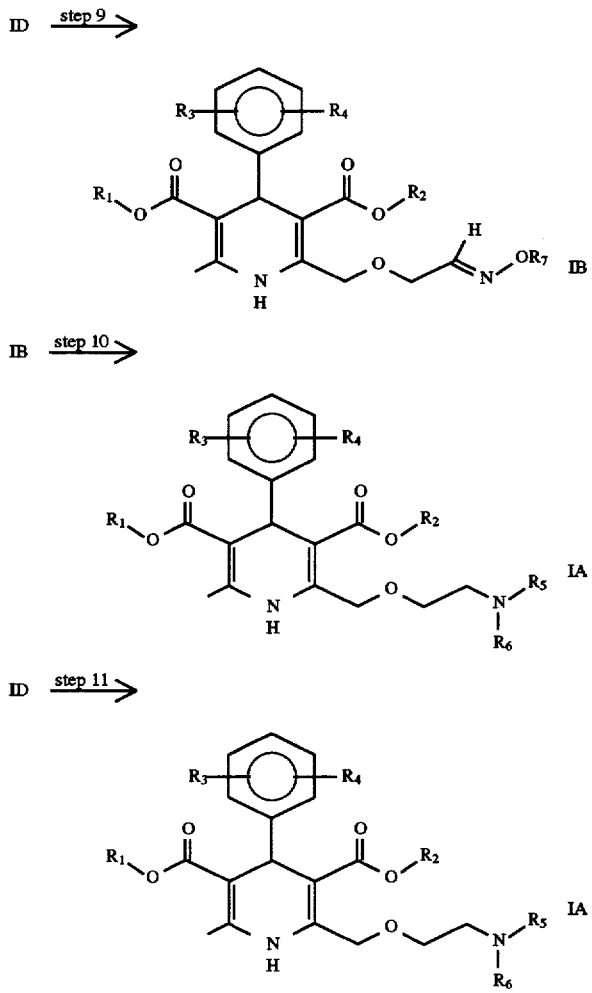

The aldehyde (ID) can be directly reduced to amine of formula (IA) ($R_5$ and $R_6$=H) by reductive amination reaction, see Borch, R. F., JACS, 1971, 93, 2897. In a typical procedure, sodium cyanohydride was added portionwise to solution of the aldehyde (ID) and ammonium acetate in an alkanol solvent such as methanol or ethanol, preferably methanol at 0° to 25° C., preferably 25° C. The reaction is stirred at the same temperature for a period of 24 to 60 hours, preferably 24 to 40 hrs. The product of formula (IA) ($R_5$ and $R_6$=H) is isolated by conventional means. Pharmaceutically acceptable salt of compound (IA) can be made by treating a solution of compound (IA) in alkanols such as methanol or ethanol and reacting the resulting solution with a pharmaceutically acceptable acid addition salts containing the pharmaceutically acceptable anions such as benzenesulfonic acid for 2 to 4 hours. Other examples of pharmaceutically acceptable anions are hydrochloride, hydrobromide, sulphate, phosphate or acid phosphate, acetate, maleate, fumarate, lactate, tartrate, citrate and gluconate salts. The resulting addition salt is isolated by conventional means such as evaporation and recrystallization. The more preferred salt of formula (IA) is the maleate salt, and the most preferred salt of formula (IA) is the benzenesulfonic acid salt.

Alternatively, the desired nitrogen atom is introduced by converting the aldehyde obtained from the above procedures to its oxime as shown in scheme III. The aldehyde (ID) is mixed with one to five equivalent of a tertiary amine and one to five equivalent of hydroxylamine hydrochloride in an alkanol solvent such as methanol or ethanol or isopropanol, preferably ethanol for a period of 8 to 24 hours, preferably 24 hrs. to give the oxime (IB). Examples of tertiary amines are triethylamine, N-methylmorpholine, N-methylpiperidine. The oxime (IB) [$R_7$=H] is isolated by conventional means. When alkoxyamine hydrochloride is used in place of hydroxylamine hydrochloride, the oxime (IB) [$R_7$=alkyl] is obtained. Alternatively, compound of formula (IB) in which $R_7$=H can be alkylated with base or acid with an appropriate alkylating agent to give oxime in which [$R_7$ is alkyl or 1-alkoxyalkyl]. For example, reaction of oxime (IB) in which $R_7$=H with pyridine hydrochloride salt and 1-methoxypropene in an inert solvent such as dichloromethane or 1,2 dichloroethane at room temperature will yield compound of formula (IB) where $R_7$ is an 1-alkoxyalkyl group. Examples of these transformations are illustrated in examples 8 and 9 of this application.

Amlodipine may be obtained directly from the oxime obtained with the above procedure. The oxime (IB) is dissolved in an alkanol solvent such as methanol, ethanol or isopropanol, preferably ethanol, and mixed with one to five equivalent of a transfer hydrogenation chemical. Examples of the latter are ammonium formate, cyclohexene, 1,3 cyclohexadiene, 1,4 cyclohexadiene. The preferred material is this reaction is ammonium formate. A hydrogenation catalyst is added portionwise to the reaction mixture and the reaction mixture was refluxed for a period of six to twenty four hours, preferably six hours to give the compounds of formula (IA) in which $R_5$ and $R_6$ are both hydrogen. Examples of hydrogenation catalyst are palladium on charcoal, palladium hydroxide on charcoal, Raney Nickel. The most preferred catalyst for this transformation is palladium hydroxide on charcoal.

Hydroxyl amine or alkoxyl amine of formula (IA) may be obtained from the oxime or alkyl oxime (IB) by modifying the reduction conditions. The oximes of general formula (IB) in which $R_7$ is hydrogen, alkyl or 1-alkoxyalkyl, are reduced with two to five equivalents of diborane-tetrahydrofuran complex, sodium borohydride or sodium cyanohydride in an ethereal solvent such as tetrahydrofuran or in an organic acid such as acetic acid to give compounds of formula (IA) in which $R_5$ is hydrogen and $R_6$ is hydroxy or alkoxy, or $R_5$ is hydroxy or alkoxy and $R_6$ hydrogen. The preferred reducing agent is sodium cyanohydride in acetic acid (Gribble and Nutaitis, Org. Prep. Proc. Int., 1985, 17, 317 and Sternbach and Jamison, Tetrahedron Lett. 1981, 22, 3331).

Preferred compounds are compounds:
(i) of formula IA wherein $R_3$ is hydrogen, $R_4$ is chloro at the 2 position, $R_1$ is methyl, $R_2$ is ethyl, $R_5$ is hydrogen and $R_6$ is hydroxy.

(ii) of formula IB wherein $R_3$ is hydrogen, $R_4$ is chloro at the 2 position, $R_1$ is methyl, $R_2$ is ethyl, $R_7$ is hydrogen.

(iii) of formula ID wherein $R_3$ is hydrogen, $R_4$ is chloro at the 2 position, $R_1$ is methyl, and $R_2$ is ethyl.

(iv) of formula IE wherein $R_3$ is hydrogen, $R_4$ is chloro at the 2 position, $R_1$ is methyl, and $R_2$ is ethyl.

In another aspect the invention relates to new N-substituted bicyclic 4-hydropyridines of formula (XXIV) and bicyclic N-substituted 4,5-dihydropyridines of formula (XXI) and (XXII)

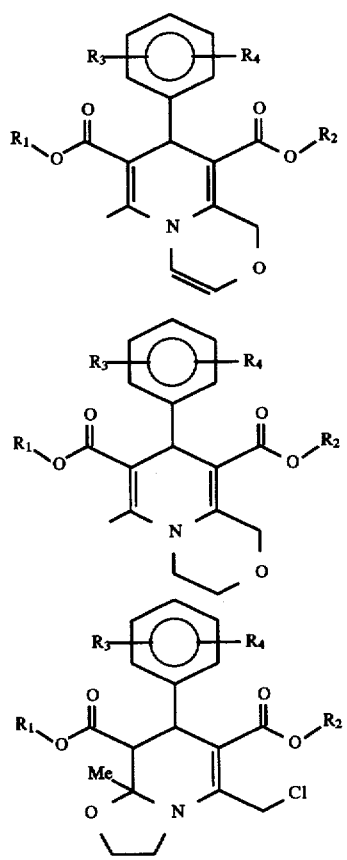

wherein $R_1$, $R_2$, $R_3$, $R_4$ are as defined above.

The compounds of formula (XXIV) are prepared by the Hantzch synthesis as shown in the following Scheme V:

Scheme V

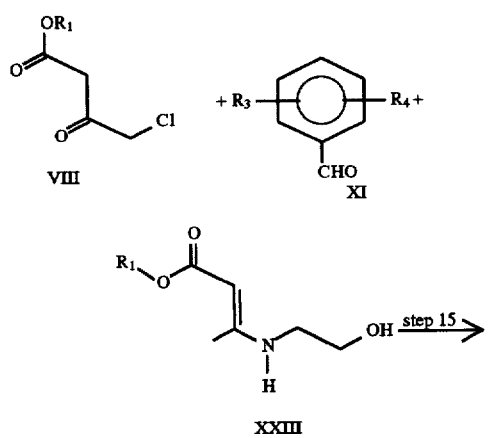

-continued
Scheme V

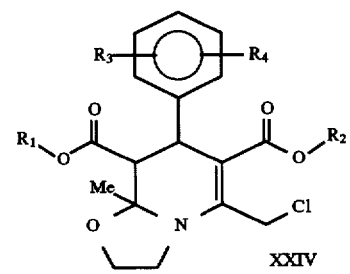

The compounds of formula (XXI) and (XXII) are prepared as shown by the following equation:

Scheme IV

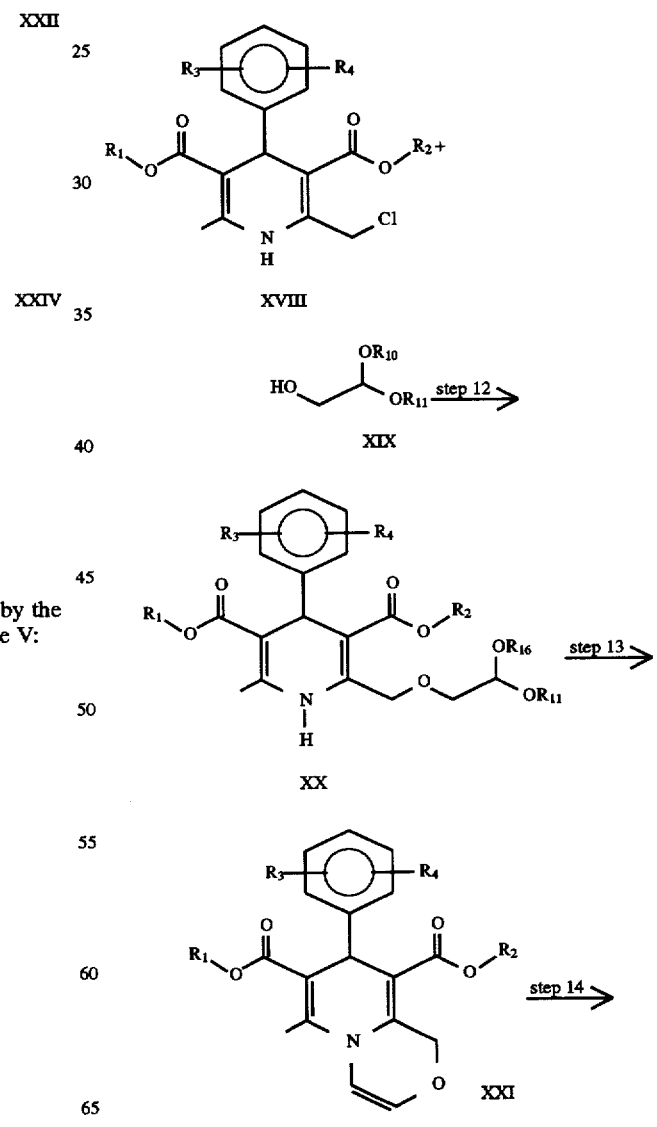

-continued
Scheme IV

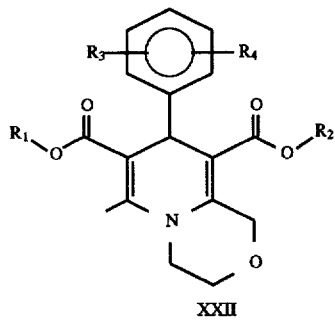

XXII

In a typical procedure the bicyclic 4-hydropyridine (XXI) was produced by mixing alcohol (XIX) with two to four equivalent of sodium hydride in inert solvent such as tetrahydrofuran or dimethylformamide and then adding the ethanolamine of formula (XVIII) to give the ether derivative of formula (XX). The product is isolated by conventional means.

The masked aldehyde (XX) is refluxed in an aqueous acidic solution for two to ten hours. Examples of an acid solution are dilute hydrochloric acid in a mixture of THF and water, dilute sulfuric acid solution in a mixture of dimethoxyethane and water, p-toluenesulfonic acid solution in toluene. Compound (XXI) is isolated by conventional means. Reduction of the —N—CH=CH—O— double bond was realised by dissolving (XXI) in an alkanol such as ethanol or methanol and hydrogenating over 10% palladium on charcoal for 6 to 24 hours at 1 to 3 atmosphere of hydrogen to give compound (XXII) such conditions are just an example of the conditions to carry out this transformation and other traditional methods can also be used. Such as Raney Ni in a mixture of chloroform and alkanol, transfer hydrogenation conditions such as 10% Pd/C and ammonium formate in refluxing alkanol. The product (XXII) is isolated by conventional means.

EXAMPLE 1

4,5-Bis-[4-(2-chlorophenyl)-3-ethoxycarbonyl-5-methoxycarbonyl-6-methyl-1,4-dihydro-2-pyridyl-methoxymethyl]-2,2-dimethyl-[1,3]dioxolane (XIII)

A mixture of 4-[5-(3-ethoxycarbonyl-2-oxo-propoxymethyl)-2,2-dimethyl-[1,3]dioxolan-4-ylmethoxy]-3-oxo-butyric acid ethyl ester (IX, 2.7 g), methyl 3-aminocrotonate (XII, 1.48 g) and 2-chlorobenzaldehyde (XI, 1.8 g) in ethanol (50 mL) was refluxed for 24 h. On cooling to room temperature, ethanol was removed under reduced pressure. The residue was purified by flash chromatography on silica gel (grade 9385, Merck, 230–400 mesh, 60 Å) using a mixture of hexane and ethyl acetate (9:1, 8:2; 500 mL each; 7:3, 6:4; 1L each; and 1:1; 500 mL) as eluent, thereby affording the title compound (XIII 2.5 g) and the mono condensed product, 2-[5-(3-ethoxycarbonyl-2-oxo-propoxymethyl)-2,2-dimethyl-[1,3]dioxolan-4-ylmethoxymethyl]-1,4-dihydro-6-methyl-3,5-pyridinedicarboxylic acid 3-ethyl 5-methyl ester (XIV, 1.95 g). Compound (XIII). m.p. 61.5°–62.8° C.; IR (KBr, cm$^{-1}$): 3374, 1691, 1647, 1609); MS (ESI): 859[M+H]$^+$, 858[M]$^+$, 857[M–H]$^+$ Compound (XIV). m.p. 60.0°–61.2° C.; IR (KBr, cm$^{-1}$): 3404, 1733, 1695, 1645, 1609;

EXAMPLE 2

4-[5-(3-Ethoxycarbonyl-2-oxo-propoxymethyl)-2,2-dimethyl-[1,3]dioxolan-4-ylmethoxy]-3-oxo-butyric acid ethyl ester (IX)

To a suspension of sodium hydride (4.0 g, 60% dispersion in oil) in tetrahydrofuran (150 mL) under a nitrogen atmosphere was added a solution of 2,2-dimethyl-[1,3]dioxolane-4,5-dimethanol (VII, 4.05 g) in tetrahydrofuran (25 mL) over 2 min at room temperature, followed by solid tetrabutylammonium hydrogen sulfate (0.4 g). The resulting mixture was cooled in an ice bath and a solution of ethyl 4-chloroacetoacetate (VIII, 8.1 g) in tetrahydrofuran (25 mL) was added dropwise over a period of 15 min. The reaction mixture was warmed to room temperature over 1 h then refluxed for 6 h. On cooling to room temperature, the reaction mixture was quenched with 1N hydrochloric acid (20 mL) and volatile materials were removed under reduced pressure. The aqueous phase was extracted with ethyl acetate (3×30 mL). The combined organic fractions was washed with brine, dried (sodium sulfate), filtered and concentrated in vacuo. The residue was purified by flash chromatography on silica gel (grade 9385, Merck, 230–400 mesh, 60 Å) using a mixture of hexane and ethyl acetate (8:2, 7:3 and 6:4; 500 mL each) as eluent, thereby affording the title compound (IX 4.5 g) as an oil and the mono O-alkylated compound, 4-(2-chlorophenyl)-2-(5-hydroxymethyl-2,2-dimethyl-[1,3]dioxolan-4-ylmethoxy-methyl-1,4-dihydro-6-methyl-3,5-pyridinedicarboxylic acid 3-ethyl 5-methyl ester (X, 1.95 g). Compound IX. IR (neat, cm$^{-1}$): 1723, 1636; MS (CI): 436 (100%, [M+NH$_4$]$^+$). Compound X. IR (neat, cm$^{-1}$): 3455, 1734;

EXAMPLE 3

1,4-Bis-[4-(2-chlorophenyl)-3-ethoxycarbonyl-5-methoxycarbonyl-6-methyl-1,4-dihydro-2-pyridyl-methoxy]-butane-2,3-diol (IE)

A solution of 4,5-Bis-[4-(2-chlorophenyl)-3-ethoxycarbonyl-5-methoxycarbonyl-6-methyl-1,4-dihydro-2-pyridyl-methoxymethyl]-2,2-dimethyl-[1,3]dioxolane (XIII, 1.9 g) and p-toluenesulfonic acid monohydrate (0.5 g) in methanol (50 mL) was stirred at room temperature for 20 h. The reaction mixture was then neutralized using triethylamine (2 mL). Volatile materials were removed under reduced pressure. The residue was taken up in ethyl acetate (50 mL) and the organic phase was washed successively with dilute hydrochloric acid (25 mL) and brine (25 mL), then dried (sodium sulfate), filtered and concentrated in vacuo. The residue was purified by flash chromatography on silica gel (grade 9385, Merck, 230–400 mesh, 60 Å) using a mixture of hexane and ethyl acetate (1:1; 500 mL) followed by dichloromethane and methanol (9:1; 500 mL) as eluent, thereby giving the title compound (IE 1.5 g). $^1$H-NMR (CDCl$_3$) δ (ppm): 1.26 (t, 3H, J=7.1 Hz), 2.35 (s, 3H), 3.63 (s, 3H), 3.73 (br,2H), 3.96 (br, 1H), 4.08 (q, 2H, J=7.1 Hz), 5.42 (s, 1H), 7.00–7.45 (m, 5H); $^{13}$C-NMR (CDCl$_3$) δ (ppm): 14.2, 19.2, 37.5, 50.7, 59.8, 68.4, 70.6, 73.4, 101.9, 103.9, 126.8, 127.4, 129.3, 131.5, 132.5, 144.0, 144.9, 145.5, 167.2, 168.0; MS (ESI): 817[M+H]$^+$, 816[M]$^+$, 815 [M–H]$^+$; m.p. 76.5°–78.0° C.; IR (KBr, cm$^{-1}$): 3424, 1689.

EXAMPLE 4

4-(2,2-Dimethyl-[1,3]dioxolan-4-ylmethoxy)-3-oxo-butyric acid ethyl ester (XVI)

To a suspension of sodium hydride (55 g, 60% dispersion in oil) in tetrahydrofuran (1L) under a nitrogen atmosphere was added a solution of 2,2-dimethyl-[1,3]dioxolane-4-methanol (XV, 102.4 g) in tetrahydrofuran (250 mL) over 15 min at room temperature. The resulting mixture was cooled in an ice bath and a solution of ethyl 4-chloroacetoacetate (VIII, 102.9 g) in tetrahydrofuran (250 mL) was added dropwise over a period of 1 h. The reaction mixture was stirred at room temperature for 20 h. The reaction mixture was then quenched with water (100 mL) and tetrahydrofuran was removed under reduced pressure. The aqueous phase was extracted with ethyl acetate (3×250 mL). The combined organic fractions was dried (sodium sulfate), filtered and concentrated in vacuo. The residue was purified by flash chromatography on silica gel (grade 9385, Merck, 230–400 mesh, 60 Å) using a mixture of hexane and ethyl acetate (9:1 and 8:2; 2L each) as eluent, thereby affording the title compound (XVI, 81.6 g). IR (neat, cm$^{-1}$): 1736. (Alker, D. J. Med. Chem. 1991, 34, 19).

EXAMPLE 5

4-(2-Chlorophenyl)-2-methyl-6-(2-oxo-ethoxymethyl)-1,4-dihydro-3,5-pyridinedicarboxylic acid 5-ethyl 3-methyl ester (ID)

(a) To an ice-cooled solution of 4-(2-chlorophenyl)-2-(2,3-dihydroxypropoxymethyl)-1,4-dihydro-6-methyl-3,5-pyridinedicarboxylic acid 3-ethyl 5-methyl ester (IC, 13.0 g) in methanol (150 mL) was added a solution of sodium periodate (7.6 g) dissolved in water (100 mL) dropwise over 15 min. After stirring for 10 min, a saturated solution of ammonium chloride (25 mL) was added. Volatile materials were removed under reduced pressure, then ethyl acetate (200 mL) and water (100 mL) were added. The organic layer was separated and the aqueous layer was twice extracted with ethyl acetate (50 mL). The combined organic fractions was washed with brine, dried (sodium sulfate), filtered and concentrated in vacuo to afford the title compound (11.8 g). Thin layer chromatography and proton NMR spectrum showed the crude title compound (ID) was sufficiently pure.
(b) In a similar fashion, the cleavage of 1,4-Bis-[4-(2-chlorophenyl)-3-ethoxycarbonyl-5-methoxycarbonyl-6-methyl-1,4-dihydro-2-pyridyl-methoxy]-butane-2,3-diol (IE, 0.4 g) with sodium periodate (0.15 g) afforded the title compound (ID 0.37 g). $^1$H-NMR(CDCL$_3$) δ (ppm): 1.19 (t, 3H, J=7.1 Hz), 2.38 (s, 3H), 3.48–3.68 (m,2H), 3.62 (s, 3H), 4.04 (q, 2H, J=7.1 Hz), 4.84 (m, 2H), 5.42 (s, 1H), 7.00–7.45 (m,5H),9.73 (s, 1H); $^{13}$C-NMR (CDCL$_3$) δ (ppm): 14.2, 19.3, 37.3, 50.7, 59.9, 69.1, 76.6, 73.4, 102.1,103.9, 126.8, 127.4, 129.3, 131.4, 132.4, 143.9, 144.2, 145.6, 167.1,167.9, 198.1; HRMS: calc. for C$_{20}$H$_{22}$ClNO$_6$407.1137 found 407.1119; m.p. 57.4°–58.3° C.; IR (KBr, cm$^{-1}$): 1700, 1692, 1648, 1607.

EXAMPLE 6

4-(2-Chlorophenyl)-2-(2-hydroxyimino-ethoxymethyl)-1,4-dihydro-6-methyl-3,5-pyridinedicarboxylic acid 3-ethyl 5-methyl ester (IBa)

(a) A mixture of 4-(2-chlorophenyl)-2-methyl-6-(2-oxo-ethoxymethyl)-1,4-dihydro-3,5-pyridinedicarboxylic acid 5-ethyl 3-methyl ester (ID, 6.2 g), hydroxylammonium hydrochloride (1.27 g) and triethylamine (1.85 g) in methanol (100 mL) was stirred at room temperature for 6 h. Methanol was removed under reduced pressure and the residue was dissolved in ethyl acetate (200 mL) and water (200 mL). With vigorous stirring, the pH of the mixture was adjusted to 10 with aqueous 1N sodium hydroxide solution. After stirring for a further 15 min, the organic layer was collected, dried (sodium sulfate), filtered and concentrated in vacuo. The residue was recristallized from ether and hexane to give the title compound IB (6.1 g). HRMS: calc. for C$_{20}$H$_{23}$ClN$_2$O$_6$ 422.1245 found 422.1248; m.p. 161.4°–162.2° C.; IR (KBr, cm$^{-1}$): 3446, 3379, 1698, 1671, 1601.

(b) In a similar manner, the O-alkylated oximes are prepared from (ID) starting with the corresponding O-alkylhydroxylamine hydrochlorides.

EXAMPLE 7

4-(2-Chlorophenyl)-2-(2-methoxyimino-ethoxymethyl)-1,4-dihydro-6-methyl-3,5-pyridinedicarboxylic acid 3-ethyl 5-methyl ester (IBb)

To an ice-cooled solution of 4-(2-chlorophenyl)-2-(2-hydroxyimino-ethoxymethyl)-1,4-dihydro-6-methyl-3,5-pyridinedicarboxylic acid 3-ethyl 5-methyl ester (IBa, 3 g) in dimethylsulfoxide (20 mL) and tetrahydrofuran (20 mL) was added solid potassium hydroxide (0.4 g) and triethylamine (0.72 g), followed by dropwise addition of iodomethane (4.0 g) over a period of 30 min. After stirring for 3 h, volatile materials were removed under reduced pressure. After diluting the residue with ethyl acetate (100 mL), the organic phase was successively washed with dilute hydrochloric acid (25 mL) and brine (25 mL), then dried (sodium sulfate), filtered and concentrated in vacuo. The residue was purified by flash chromatography on silica gel (grade 9385, Merck, 230–400 mesh, 60 Å) using a mixture of hexane and ethyl acetate (100%, 9:1, and 8:2; 500 mL each) as eluent, thereby affording the title compound (IBb 1.86 g). HRMS: calc. for C$_{21}$H$_{25}$ClN$_2$O$_6$ 436.1401 found 436.1408; IR (neat, cm$^{-1}$): 3346, 1690, 1649, 1609.

EXAMPLE 8

4-(2-Chlorophenyl)-2-[2-(1-methoxy-1-methylethoxyimino-ethoxymethyl]-1,4-dihydro-6-methyl-3,5-pyridinedicarboxylic acid 3-ethyl 5-methyl ester (IBc)

To a solution of 4-(2-chlorophenyl)-2-(2-hydroxyimino-ethoxymethyl)-1,4-dihydro-6-methyl-3,5-pyridinedicarboxylic acid 3-ethyl 5-methyl ester (IBa, 0.845 g) in dichloromethane (15 mL) was added solid pyridine hydrochloride (0.23 g) and methoxypropene (0.58 g). After stirring for 24 h, solvent was removed under reduced pressure and the residue was purified by flash chromatography on silica gel (grade 9385, Merck, 230–400 mesh, 60 Å) using a mixture of hexane and ethyl acetate (95:5, 9:1, and 8:2;300 mL each) as eluent, thereby affording the title compound (IBc 0.79 g). HRMS: calc. for C$_{24}$H$_{31}$ClN$_2$O$_7$ 494.1820 found 494.1823; IR (KBr, cm$^1$): 1691, 1649, 1609.

EXAMPLE 9

2-[(2-Aminoethoxy)methyl]-4-(2-chlorophenyl)-1,4-dihydro-6-methyl-3,5-pyridinedicarboxylic acid 3-ethyl 5-methylester (IAa)

(a) A mixture of4-(2-chlorophenyl)-2-methyl-6-(2-oxo-ethoxymethyl)-1,4-dihydro-3,5-pyridinedicarboxylic acid 5-ethyl 3-methyl ester (ID, 7.34 g), ammonium acetate (14.40 g) and sodium cyanohydride (176 g) in methanol (200 mL) was stirred under a nitrogen atmosphere for 20 h. Concentrated hydrochloric acid was then added dropwise until the pH of the mixture was<2. Volatile materials were removed under reduced pressure and the residue was diluted with water (200 mL). The aqueous layer was washed with ethyl acetate (50 mL). The aqueous layer was collected and basified with solid potassium hydroxide until the pH of the solution was>12. The crude title product was extracted with ethyl acetate (3×150 mL). The combined organic fractions was dried (sodium sulfate), filtered and evaporated to dryness. The residue was crystallized from ether and hexane thereby affording the title product (IAa 3.5 g). $^1$H-NMR (CDCl$_3$) δ (ppm): 1.28 (t, 3H, J=7.1 Hz), 1.26 (br, 2H, NH$_2$), 2.38 (s, 3H), 3.25–3.85 (m, 4H), 3.60 (s, 3H), 4.10 (q, 2H, J=7.1 Hz), 4.80 (m, 2H), 5.40 (s,1H),7.02–7.49 (m, 4H), 7.78 (br, 1H, NH); HRMS: calc. for C$_{20}$H$_{25}$ClN$_2$O$_5$ 408.1452 found 408.1439; m.p. 62.8°–63.9° C.; IR (KBr, cm$^{-1}$): 1690, 1645, 1609.

(b) A mixture of 4-(2-chlorophenyl)-2-(2-hydroxyimino-ethoxymethyl)-1,4-dihydro-6-methyl-3,5-pyridinedicarboxylic acid 3-ethyl 5-methyl ester (IBa, 150 mg), palladium hydroxide on carbon (10 mg) and ammonium formate (224 mg) in methanol (10 mL) was refluxed for 5 h under a nitrogen atmosphere. On cooling to room temperature, the mixture was filtered through a pad of celite. The filtrate was concentrated in vacuo. Purification of the residue by flash chromatography on silica gel (grade 9385, Merck, 230–400 mesh, 60 Å) using a solvent mixture of dichloromethane and methanol (9:1; 100 mL), and dichloromethane, methanol and ammonium hydroxide (90:10:1; 500 mL) as eluent afforded the title compound (IAa 88 mg).

EXAMPLE 10

4-(2-Chlorophenyl)-2-[(2-N-hydroxyamino)ethoxymethyl]-1,4-dihydro-6-methyl-3,5-pyridinedicarboxylic acid 3-ethyl 5-methyl ester (IAb)

(a) To an ice cooled solution of 4-(2-chlorophenyl)-2-(2-hydroxyimino-ethoxymethyl)-1,4-dihydro-6-methyl-3,5-pyridinedicarboxylic acid 3-ethyl 5-methyl ester (IBa, 422.5 mg) in 20 mL dichloromethane was added 10 mL of glacial acetic acid followed by sodium cyanohydride (158 mg). After stirring for 30 min, the mixture was poured onto 3N sodium hydroxide solution (25 mL) and crashed ice. The pH of the solution was adjusted to about 10. The organic phase was collected. The aqueous phase was twice extracted with dichloromethane (2×20 mL). The combined organic phase was dried (sodium sulfate), filtered and concentrated in vacuo. Recristallization from ether and hexane afforded the title compound (IAb 390 mg). $^1$H-NMR (CDCl$_3$) δ (ppm): 1.17 (t, 3H, J=7.1 Hz), 2.30 (s, 3H), 3.17 (t, 2H, J=4.6 Hz), 3.60 (s, 3H), 3.75 (t, 2H, J=4.4 Hz), 4.05 (q, 2H, J=7.1 Hz), 4.70 (d, 1H, J=16.2 Hz), 4.80 (d, 1H, J =16.2 Hz),5.39 (s, 1H), 7.00–7.45 (m, 5H), 7.46 (s, 1H, NH); $^{13}$C-NMR (CDCl$_3$) δ (ppm): 14.2, 19.1, 37.3, 50.7, 52.8, 59.8, 67.7, 68.1,101.5, 103.8, 126.8, 127.3, 129.2, 131.5, 132.4, 144.2, 145.4, 145.7, 167.2, 168.0; MS (CI): 439[M+NH$_3$]$^+$, 424 [M]$^+$, 423 [M−H]$^+$; M.p. 78.9°–79.8° C.; IR(KBr, cm$^{-1}$): 3391, 3257, 1705, 1674, 1645, 1604.

(b) In a similar fashion, the reduction of the N-alkoxyimines give the corresponding N-alkoxy amines.

EXAMPLE 11

4-(2-Chlorophenyl)-2-(2-2-dimethoxy-ethoxymethyl)-1,4-dihydro-6-methyl-3,5-pyridinedicarboxylicacid 3-ethyl 5-methyl ester (XX)

To a suspension of sodium hydride (8.0 g, 60% dispersion in oil) in tetrahydrofuran (400 mL) under a nitrogen atmosphere was added a of 2,2-dimethoxyethanol (XIX, 10.61 g, prepared according to the procedure described by Machida, S. et al. in Tetrahedron 1991, 47, 3737) followed by a solution of 2-(2-chloromethyl)-4-(2-chlorophenyl)-1,4-dihydro-6-methyl-3,5-pyridinedicarboxylic acid 3-ethyl 5-methyl ester (XVIII, 34.8 g, prepared as described by Cupka and Svetlik, Synth. Commun. 1986, 16, 529) in tetrahydrofuran (50 mL). The reaction mixture was stirred at room temperature for 16 h. The reaction mixture was worked up as described in example 5. The residue was purified by flash chromatography on silica gel to afford the title compound (XX 10.0 g). HRMS: calc. for C$_{22}$H$_{28}$ClNO$_7$ 453.1554 found 453.1564; Elemental Analysis (%): calc (found) C 58.21 (58.59), H 6.22 (6.21), N 3.09 (3.00); M.p. 71.0°–72.2° C.; IR (KBr, cm$^{-1}$): 3308, 1696, 1684, 1640, 1602.

EXAMPLE 12

8-(2-Chlorophenyl)-6-methyl-1,8-dihydropyrido [2,1-c][1,4]-oxazine-7,9-dicarboxylic acid 9-ethyl 7-methyl ester (XXI)

To a solution of 4-(2-chlorophenyl)-2-(2,2-dimethoxy-ethoxymethyl)-1,4-dihydro-6-methyl-3,5-pyridinedicarboxylic acid 3-ethyl 5-methyl ester (XX, 9.2 g) in tetrahydrofuran (200 mL) was added 3N hydrochloric acid (40 mL). The mixture was then refluxed for 4 h. On cooling to room temperature, tetrahydrofuran was removed under reduced pressure and the residue taken up in ethyl acetate (200 mL). The organic phase was washed with brine, dried (sodium sulfate), filtered and concentrated in vacuo. The residue was purified by flash chromatography on silica gel (grade 9385, Merck, 230–400 mesh, 60 Å) using a solvent mixture of hexane and ethyl acetate as eluent (90:10; 1L) as eluent to afford the title compound (XXI 5.2 g). $^1$H-NMR (CDCl$_3$) δ (ppm): 1.22 (t, 3H, J=7.1 Hz), 2.43 (s, 3H), 3.68 (s, 3H), 4.12 (q, 2H, J=7. 1 Hz),4,60(d,1H, J=13.5 Hz), 5.48 (s, 1H), 5.70 (d, 1H, J=13.8 Hz), 6.21 (d, 1H, J=4.7 Hz), 6.30(d, 1H, J=4.6 Hz), 7.07–7.28 (m, 4H); $^{13}$C-NMR (CDCl$_3$) δ (ppm): 14.1, 15.7, 36.6, 51.2, 60.6, 63.5, 105.8, 106.7, 107.8, 127.3, 127.8, 129.5, 130.4, 131.8, 132.5 139.2, 142.0, 143.4, 166.4, 168.1; HRMS: calc. for C$_{20}$H$_{20}$ClN$_2$O$_5$ 389.1030 found 389.1020; Elemental Analysis (%): calc. (found) C 61.62 (61.78), H 5.17 (5.27), N 3.59 (3.51); M.p. 126.0°–126.8° C.; IR (KBr, cm$^{-1}$): 1693, 1662, 1645, 1581.

EXAMPLE 13

8-(2-Chlorophenyl)-6-methyl-1,3,4,8-tetrahydro-pyrido[2,1-c][1,4]-oxazine-7,9-dicarboxylic acid 9-ethyl 7-methyl ester (XXII)

A mixture of 8-(2-chlorophenyl)-6-methyl-1,3,4,8-tetrahydro-pyrido[2, 1-c][1,4]-oxazine-7,9-dicarboxylic acid 9-ethyl 7-methyl ester (XXI, 389.5 mg), ammonium acetate (630 mg) amd palladium on carbon (10 mg) in ethanol (20 mL) was heated at 60° C. for 1 h. The mixture was filtrated through a pad of Celite and washed through with ethyl acetate. Solvents were removed in vacuo and the residue was recristallized from ether and hexane to afford the title compound (XXII 350 mg). $^1$H-NMR (CDCl$_3$) δ (ppm): 1.28 (t, 3H, J=7.1 Hz), 2.54 (s, 3H), 3.46 (d of t, 2H), 3.72 (s, 3H), 3.9–4.2(m,6H), 4.95 (d, 1H, J=17.3 Hz), 5.08 (s, 1H), 5.15 (d, 1H, J=17.3 Hz), 7.10–7.28(m,4H); HRMS: calc. for C$_{20}$H$_{22}$ClNO$_5$ 391.1187 found 391.1186; M.p. 141.4°–142.6° C.; IR (KBr, cm$^{-1}$): 1703, 1680, 1640, 1566.

EXAMPLE 14

5-Chloromethyl-7-(2-chlorophenyl)-8a-methyl-3,7,8, 8a-tetrahydro-2H-oxazolo[3,2-a]pyridine-6,8-dicarboxylic acid 6-ethyl 8-methyl ester (XXIV)

A mixture of 2-chlorobenzaldehyde (XI, 57.0 g), ethyl 4-chloroacetoacetate (VIII, 69.3 g) and 3-(2- hydroxyethylamino)-but-2-enoic acid methyl ester (XXIII, 63.2 g) in methanol (800 mL) was stirred at room temperature for 48 h. Methanol was removed under reduced pressure and the residue dissolved in ethyl acetate (400 mL). The organic phase was washed with brine, dried (sodium sulfate), filtered and concentrated in vacuo. Purification of the residue by flash chromatography on silica gel (grade 9385, Merck, 230–400 mesh, 60 Å) using a solvent mixture of hexane and ethyl acetate as eluent (95:5, 90:10, 85:15, 80:20, 70:30 and 60:40) as eluent afforded the title compound (XXIV 30.0 g). $^1$H-NMR (CDCl$_3$) δ (ppm): 0.80 (t, 3H, J=6.9 Hz), 1.05 (s, 3H), 3.73 (s, 3H), 3.39 (s, 1H), 3.74–4.09 (m, 4H), 4.06 (q, 2H, J=6.9 Hz), 4.51 (d, 1H, J=11.5 Hz), 4.63 (s, 1H), 5.40 (d, 1H, J=11.5 Hz), 7.12–7.40 (m, 4H); $^{13}$C-NMR (CDCl$_3$) δ (ppm): 13.6, 25.7, 39.3, 39.7, 45.8, 51.0, 51.7, 59.5, 63.4, 90.5, 98.6, 126.3, 126.8, 129.6, 129.9, 133.6, 140.7, 149.5, 167.5, 171.8; HRMS: calc. for $C_{20}H_{23}Cl_2NO_2$ 427.0953 found 427.0939; Elemental Analysis (%): calc. (found) C 56.09 (56.12), H 5.41 (5.26), N 3.27 (3.07); m.p. 141.9°–142.8° C.; IR(KBr, cm$^{-1}$): 1742, 1676, 1581, 1566.

EXAMPLE 15

3-(2-Hydroxyethylamino)-but-2-enoic acid methyl ester (XXIII)

To an ice-cooled sample of ethanolamine (6.1 g) was added methyl acetoacetate (11.6 g) dropwise. Compound (XXIII 14.5 g) was formed within 30 min (U.S. Pat. No. 1102800).

What is claimed:

1. A 1,4-dihydropyridine of the formula I:

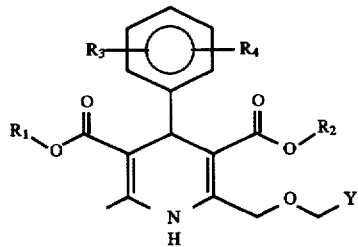

or the pharmaceutically acceptable salt thereof, wherein R$_1$ and R$_2$ are the same or different and are lower alkyl of from 1 to 5 carbon atoms including branched and straight chains; R$_3$ is hydrogen, or halogens; R$_4$ is hydrogen, or halogens; Y is selected from the group of formula II, III, V, or VI;

—CH$_2$NR$_5$R$_6$  II

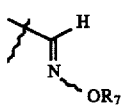  III

  V

-continued

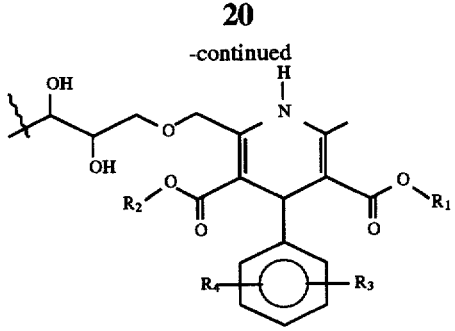  VI wherein in formula II
R$_5$ is hydroxy, alkoxy, or 1-alkoxyalkyloxy when R$_6$ is hydrogen;
R$_6$ is hydroxy, alkoxy, or 1-alkoxyalkyloxy when R$_5$ is hydrogen;
wherein in formula III
R$_7$ is hydrogen, lower alkyl, or 1-alkoxyalkyl.

2. A compound of claim 1, wherein R$_3$ is chloro at the 2-position of the phenyl ring, R$_4$ is hydrogen, R$_1$ is methyl, R$_2$ is ethyl, Y is a compound of formula III in which R$_7$ is hydrogen, lower alkyl, or 1-alkoxyalkyl.

3. A compound of claim 1, wherein R$_3$ is chloro at the 2-position of the phenyl ring, R$_4$ is hydrogen, R$_1$ is methyl, R$_2$ is ethyl, Y is a compound of formula V.

4. A compound of claim 1, wherein R$_3$ is chloro at the 2-position of the phenyl ring, R$_4$ is hydrogen, R$_1$ is methyl, R$_2$ is ethyl, Y is a compound of formula VI in which R$_3$ is chloro at the 2-position of the phenyl ring, R$_4$ is hydrogen, R$_1$ is methyl, R$_2$ is ethyl.

5. A compound of formula XXI wherein R$_1$ and R$_2$ are the same or different and are lower alkyl of from 1 to 5 carbon atoms including branched and straight chains; R$_3$ is hydrogen, chloro, or fluoro; R$_4$ is hydrogen, chloro, or fluoro

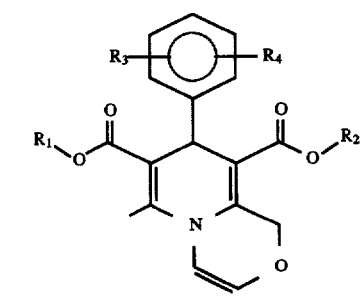  XXI

6. A compound of claim 5 wherein R$_1$ is methyl, R$_2$ is ethyl, R$_3$ is hydrogen and R$_4$ is chloro at the 2 position.

7. A compound of formula XXII wherein R$_1$ and R$_2$ are the same or different and are lower alkyl of from 1 to 5 carbon atoms including branched and straight chains; R$_3$ is hydrogen, chloro, or fluoro; R$_4$ is hydrogen, chloro, or fluoro

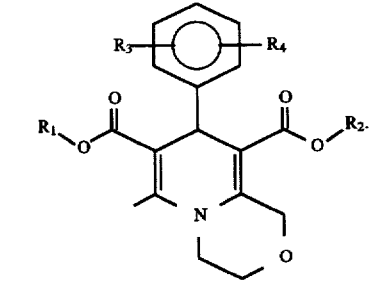  XXII

8. A compound of claim 7 wherein R$_1$ is methyl, R$_2$ is ethyl, R$_3$ is chloro at the 2 position of the phenyl ring, R$_4$ is hydrogen.

9. A compound of formula XXIV wherein $R_1$ and $R_2$ are the same or different and are lower alkyl of from 1 to 5 carbon atoms including branched and straight chains;

$R_3$ is hydrogen, chloro, or fluoro; $R_4$ is hydrogen, chloro, or fluoro

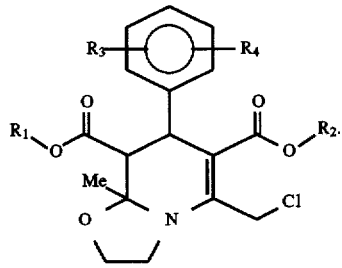

XXIV

10. A compound of claim 8 wherein $R_1$ is methyl, $R_2$ is ethyl, $R_3$ is chloro at the 2 position of the phenyl ring, $R_4$ is hydrogen.

11. 4-(2-chlorophenyl)-2-([2-N-hydroxyamino-ethoxy] methyl)-1,4-dihydro-6-methyl-3,5-pyridinedicarboxylic acid 5-ethyl 3-methyl ester.

12. A compound of formula XIV wherein $R_1$ is lower alkyl; $R_2$ is lower alkyl; $R_3$ is hydrogen, chloro, or fluoro; $R_4$ is hydrogen, chloro, or fluoro; $R_8$ is methyl, $R_9$ is methyl

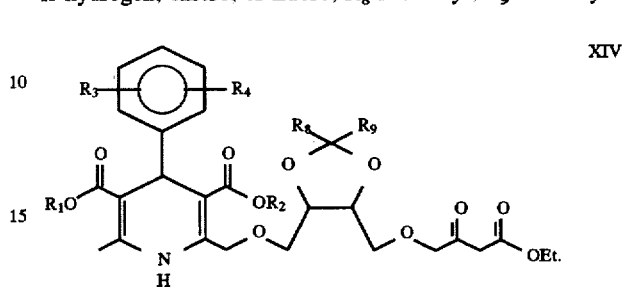

XIV

* * * * *